United States Patent
Glass et al.

(10) Patent No.: US 9,481,880 B2
(45) Date of Patent: Nov. 1, 2016

(54) METHODS OF GENOME INSTALLATION IN A RECIPIENT HOST CELL

(75) Inventors: John I. Glass, Germantown, MD (US); Nina Alperovich, Germantown, MD (US); Clyde A. Hutchison, III, La Jolla, CA (US); Carole Lartigue, Gaithersburg, MD (US); Charles E. Merryman, Sykesville, MD (US); Sanjay Vashee, Boyds, MD (US); J. Craig Venter, La Jolla, CA (US)

(73) Assignee: Synthetic Genomics, Inc., La Jolla, CA (US)

( * ) Notice: Subject to any disclaimer, the term of this patent is extended or adjusted under 35 U.S.C. 154(b) by 81 days.

(21) Appl. No.: 12/598,414

(22) PCT Filed: May 1, 2008

(86) PCT No.: PCT/US2008/062307
§ 371 (c)(1),
(2), (4) Date: Apr. 22, 2010

(87) PCT Pub. No.: WO2008/144192
PCT Pub. Date: Nov. 27, 2008

(65) Prior Publication Data
US 2011/0045592 A1     Feb. 24, 2011

Related U.S. Application Data

(60) Provisional application No. 60/927,293, filed on May 1, 2007, provisional application No. 60/927,259, filed on May 1, 2007.

(51) Int. Cl.
*C12N 15/10* (2006.01)
*C12N 15/74* (2006.01)

(52) U.S. Cl.
CPC ........... *C12N 15/10* (2013.01); *C12N 15/1079* (2013.01); *C12N 15/74* (2013.01)

(58) Field of Classification Search
CPC .. C12N 15/10; C12N 15/1079; C12N 15/74; C12N 15/8206; C12N 15/8213; C12N 15/907
See application file for complete search history.

(56) References Cited

U.S. PATENT DOCUMENTS 5,834,233 A  11/1998  Molin et al.
6,521,427 B1  2/2003  Evans

FOREIGN PATENT DOCUMENTS

AU     2006346810     2/2008

OTHER PUBLICATIONS

Lartigue et al. Science 317(5838):632-8, 2007.*
Ball et al (Nature 448(7149):32-3, 2007.*
Itaya et al Proc Natl Acad Sci U S A. 102(44):15971-6, 2005.*
Thaler et al., Bioessays, 31 (7):774-83, 2009.*
Sorek et al. Science 318(5855): 1449-52, 2007.*
Lee et al Microbiology (2008), 154, 2571-2580.*
Lee et al., Microbiology, 154(Pt 9):2571-80, 2008.*
Lartigur et al Nucleic Acids Research, 2003, 31, 22, 6610-6618.*
Akamatsu and Taguchi, "A simple and rapid method for intra- and interspecific transformation of Bacillus subtilis on solid media by DNA in protoplast lysates", *Biosci. Biotechnol. Biochem.*, 65(2):446-448 (2001).
Bheemanaik et al., "Structure, function and mechanism of exocyclic DNA methyltransferases", *Biochem. J.*, 399(2):177-190 (2006).
Janis et al., "Versatile use of oriC plasmids for functional genomics of *Mycoplasma capricolum* subsp. *capricolum*", *Appl. Environ. Microbiol.*, 71(6):2888-2893 (2005).
Kodumal et al., "Total synthesis of long DNA sequences: synthesis of a contiguous 32-kb polyketide synthase gene cluster", *Proc. Natl. Acad. Sci. USA*., 101(44):15573-15578 (2004).
Reeve et al., "Minicells of *Bacillus subtilis*", *J. Bacteriol.*, May 1973;114(2):860-873 (1973).
International Search Report (ISR) from PCT/US2008/062307.
Check, E.: "Venter aims for maximum impact with minimal genome"; Nature, 2002, vol. 420, p. 350.
Canadian Office Action issued on Feb. 4, 2016, regarding 2,702,676.

* cited by examiner

*Primary Examiner* — Anoop Singh
(74) *Attorney, Agent, or Firm* — DLA Piper LLP (US)

(57) ABSTRACT

The presently disclosed invention relates to methods of installing a genome isolated from one species (the donor) into suitably prepared cells of a second species (the recipient). Introduction of the donor genetic material into the recipient host cell effectively converts the recipient host cell into a new cell that, as a result of the operation of the donated genetic material, is functionally classified as belonging to the genus and species of the donor genetic material.

5 Claims, 15 Drawing Sheets

Figure 7:
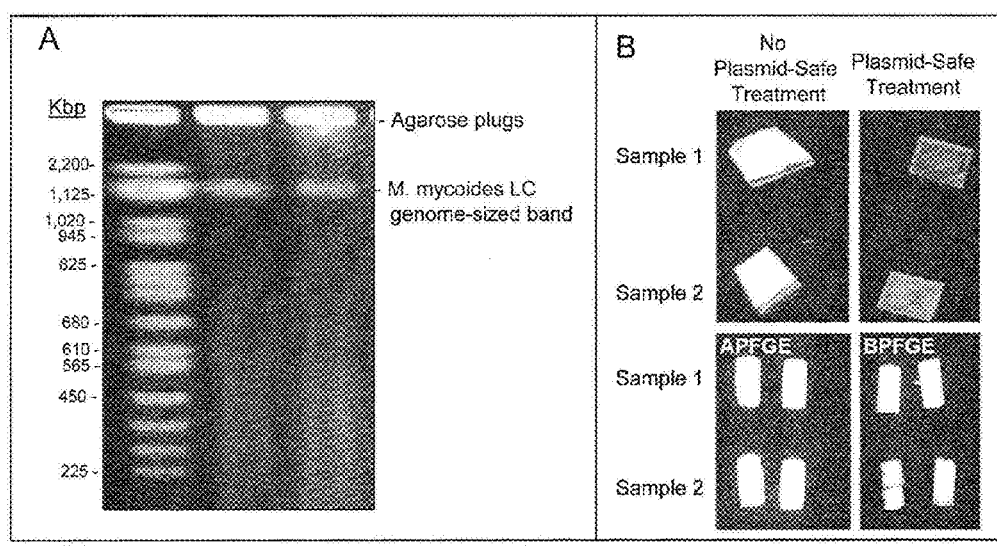

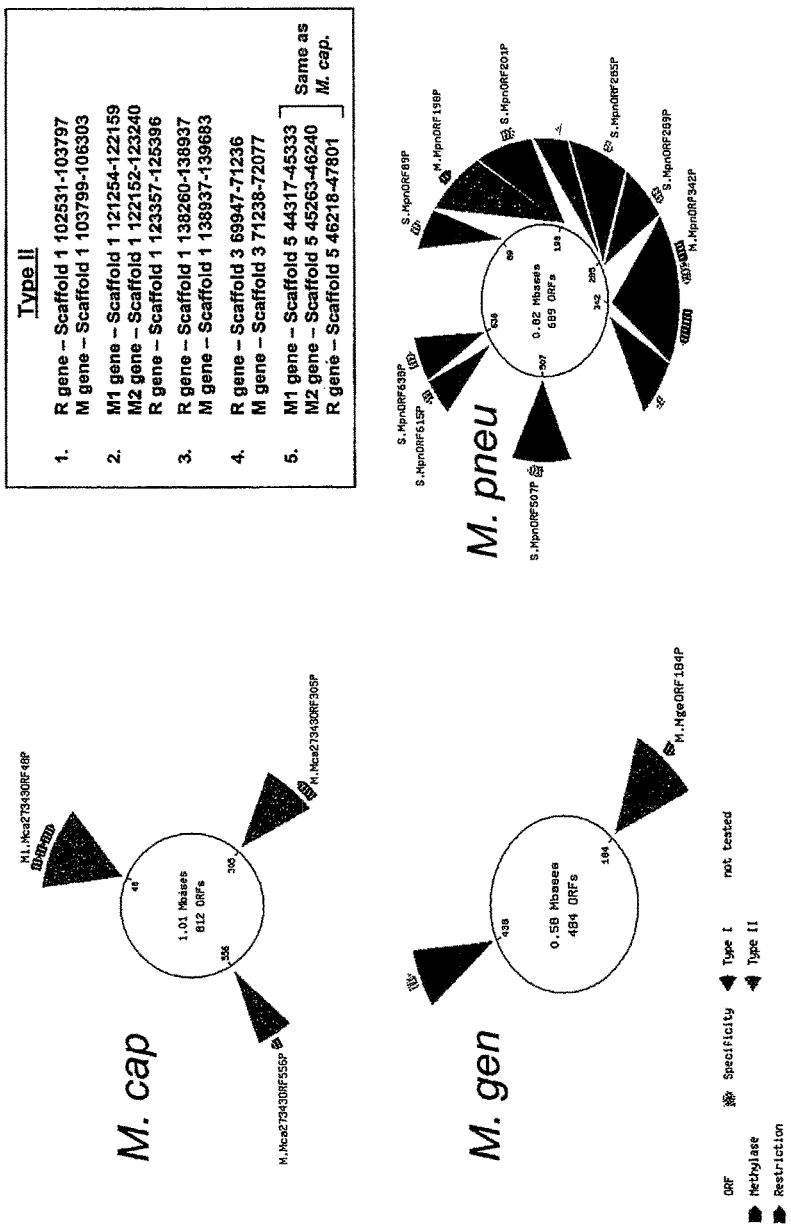
Fig. 1. Restriction modification systems encoded by *M. capricolum (M cap)*, *M. mycoides LC (M.myc LC)*, *M. genitalium (M. gen)* and *M. pneumoniae (M. pneu)*
*M. myc* LC
| | | | |
|---|---|---|---|
| | Type II | | |
| 1. | R gene – Scaffold 1 102531-103797 | | |
| | M gene – Scaffold 1 103799-106303 | | |
| 2. | M1 gene – Scaffold 1 121254-122159 | | |
| | M2 gene – Scaffold 1 122152-123240 | | |
| | R gene – Scaffold 1 123357-125396 | | |
| 3. | R gene – Scaffold 1 138260-138937 | | |
| | M gene – Scaffold 1 138937-139683 | | |
| 4. | R gene – Scaffold 3 69947-71236 | | |
| | M gene – Scaffold 3 71238-72077 | | |
| 5. | M1 gene – Scaffold 5 44317-45333 | ] | Same as *M. cap.* |
| | M2 gene – Scaffold 5 45263-46240 | | |
| | R gene – Scaffold 5 46218-47801 | | |

Fig. 2. *M. myc.* LC, *M. cap.*, *M. gen.* and *M. pneu.* genomic DNA contain adenine residues methylated at the $N^6$ position.

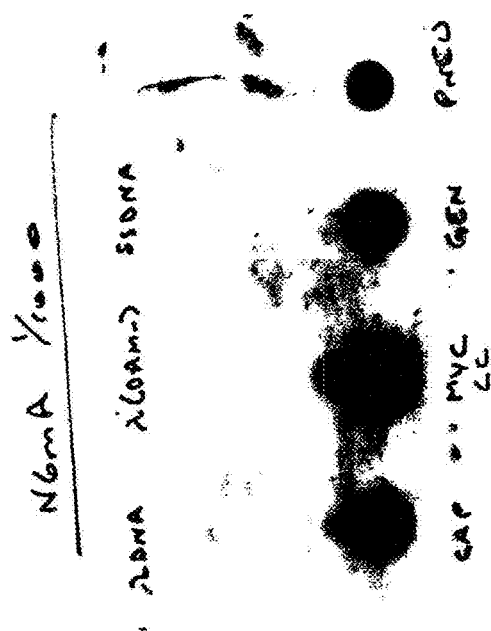

Purified genomic DNA of the indicated organisms were spotted and crosslinked by UV onto nitrocellulose and probed with an antibody that specifically recognizes adenine residues that are methylated at the $N^6$ position. The Lambda (λ) DNA serves as a positive control and the Lambda DNA isolated from an *E. coli* strain that has been deleted of the *dam* gene serves as the negative control.

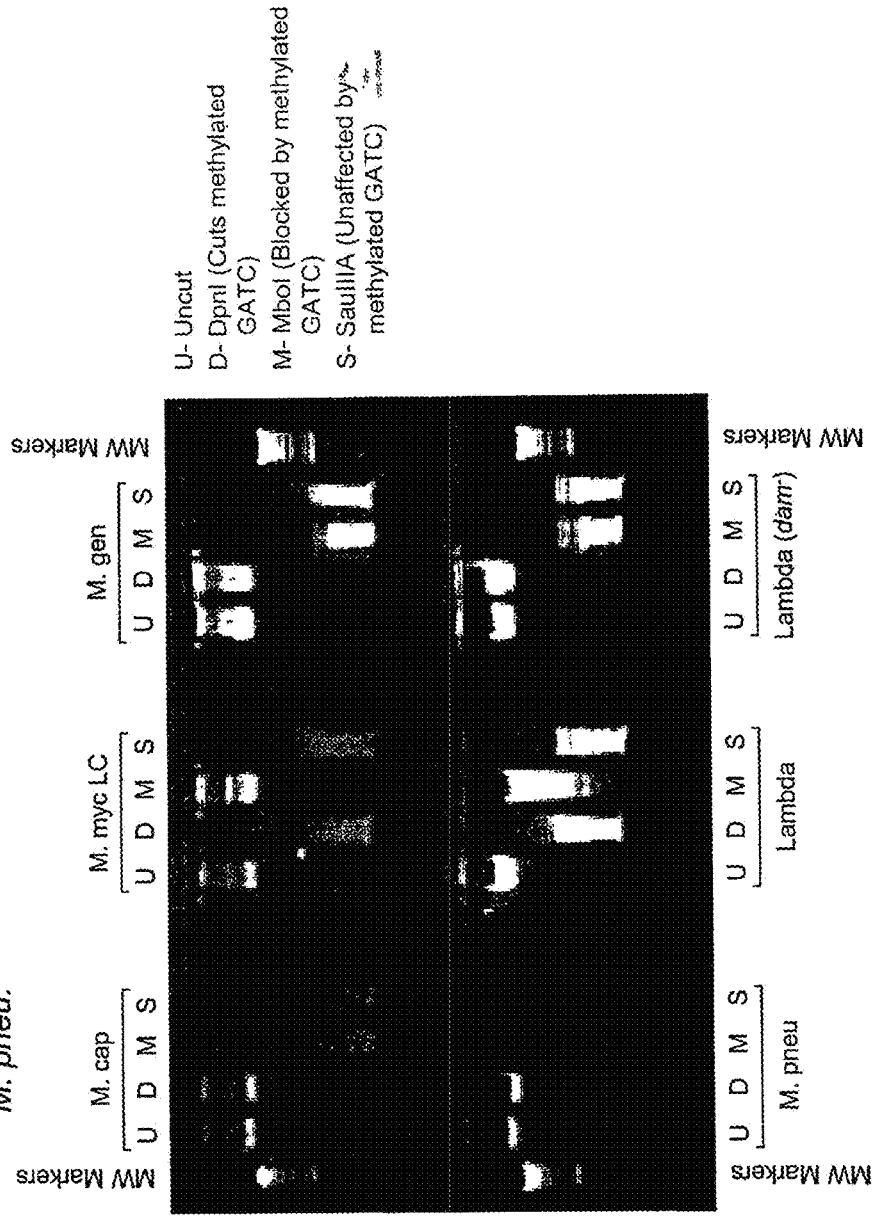
Fig. 3. *M. myc.* LC genomic DNA is methylated differently than *M. cap.*, *M. gen.* and *M. pneu.*

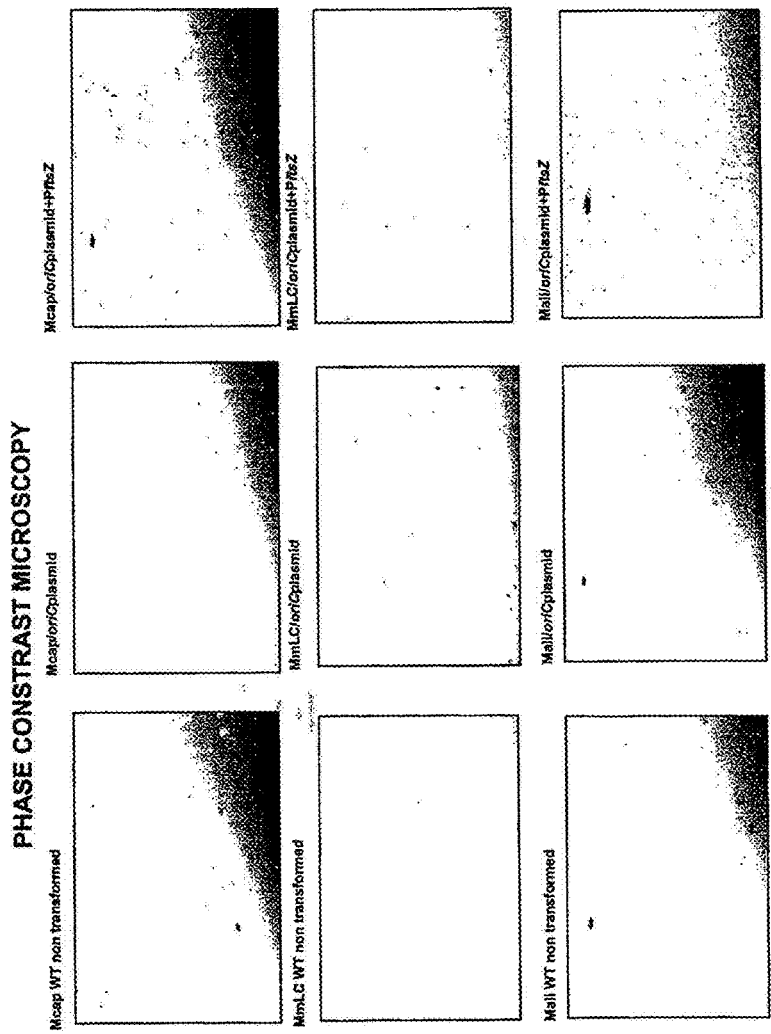
Fig. 4. Phase contrast micrographs of mycoplasma cells with altered cell shape due to the overexpresson of FtsZ

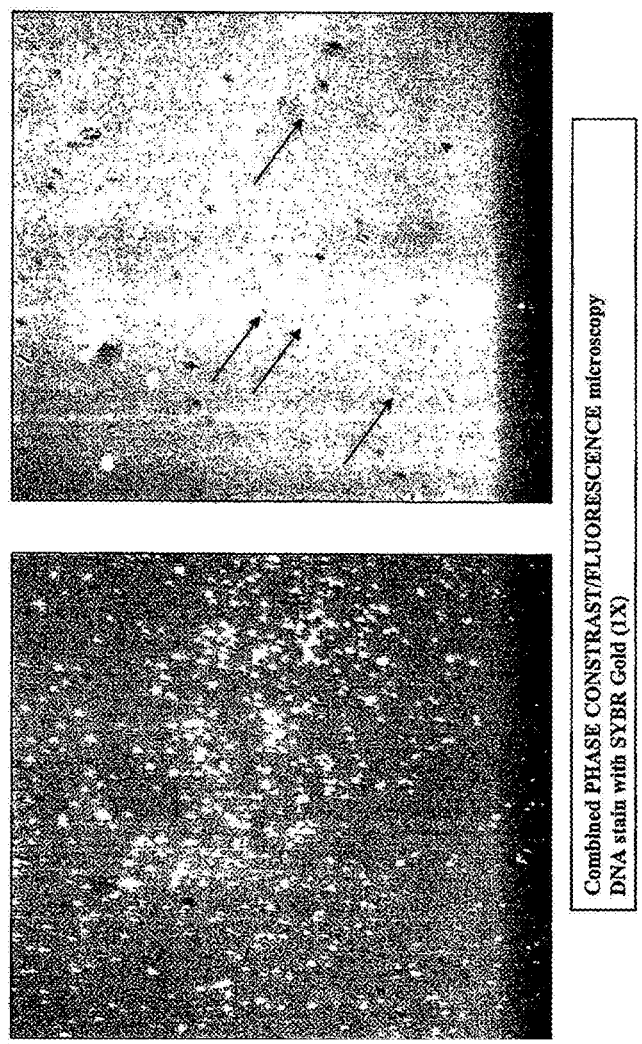
Fig. 5. Combined phase contrast and epifluorescence micrographs of *M. capricolum* cells overexpressing FtsZ protein resulting in elongated cells that may be effective recipient for transplantation of donor genomes.
Combined PHASE CONSTRAST/FLUORESCENCE microscopy
DNA stain with SYBR Gold (1X)

Figure 6. Enhanced transplantation of *M. mycoides* LC genomic DNA in the presence of the restriction enzyme Mbo I. Purified *M. mycoides* LC genomic DNA was mixed with serial dilutions of restriction enzyme Mbo I, the mixtures were transplanted into *M. capricolum* recipient cells, and transplants were recovered by plating on selective media. Natural methylation of the donor *M. mycoides* genomic DNA prevents it from being cleaved by the enzyme. In contrast, the genomic DNA of the recipient *M. capricolum* cells is sensitive to Mbo I. Co-tranplantation of the donor DNA and the enzyme selectively compromises the genomic DNA of the recipient cells and this is reflected in the number of transplants recovered. This mechanism is consistent with the fact that transplant yield increases with increasing enzyme concentration. Plate numbers are listed on the bottom of the graph. Plate 1, no added genomic DNA; plate 2, no recipient cells; plate 3, genomic DNA plus 10 ul of Mbo I; plate 4, genomic DNA plus 1 ul of Mbo I; plate 5, genomic DNA plus 0.1 ul of Mbo I; plate 6, genomic DNA plus 0.01 ul of Mbo I; plate 7, genomic DNA without Mbo I.

Figure 9

Figure 13

*M capricolum*
specific primers

*M. mycoides* LC IS1296
specific primers

Figure 15

Anti-Mcap specific polyclonal antibodies (anti-VmcE and VmcF)

| M cap WT | MmLC donor cells 2-6-24 | Transplant 11.1 |
| Transplant #10.14-S | Transplant #19.1 | Transplant #8.2-B |

Note that the dots visible for the MmLC cells and transplant cells are the negative unstained colonies.

Anti-M. mycoides specific monoclonal antibodies (anti-VchL)

| M cap WT | MmLC donor cells 2-6-24 | Transplant 11.1 |
| Transplant #10.14-S | Transplant #19.1 | Transplant #8.2-B |

METHODS OF GENOME INSTALLATION IN A RECIPIENT HOST CELL

CROSS-REFERENCE TO RELATED APPLICATIONS

This application is the national phase of PCT application PCT/US2008/062307 having an international filing date of May 1, 2008, which claims priority from provisional application No. 60/927,293 filed on May 1, 2007 and from provisional application No. 60/927,259 filed on May 1, 2007. The contents of these documents are incorporated herein by this reference in their entirety

STATEMENT OF RIGHTS TO INVENTION MADE UNDER FEDERALLY SPONSORED RESEARCH

This work was supported in part by grants from the National Institutes of Health and the Department of Defense. The U.S. government has certain rights in this invention.

TECHNICAL FIELD

The present invention relates generally to methods for genome installation in a recipient host cell.

BACKGROUND ART

Four natural processes have been described for the entry of large DNA molecules into bacterial cells. They are transformation, transduction, conjugation, and cell fusion. For none of these natural mechanisms, nor for any reported laboratory method, can a bacterial genomes be inserted into other bacterial cells resulting in new cells that have the genotype and phenotype of the input genome. Transformation of bacteria with DNA from other species is routine, but only with small segments of DNA. Using nucleoids isolated from gently lysed *Bacillus subtilis* protoplasts Akamatsu and colleagues have demonstrated same species co-transformation of distant markers. Their most recent analysis concludes that at least 30% of the 4.2 Mbp *B. subtilis* genome was recombined into the recipient cell.

SUMMARY OF THE INVENTION

In one embodiment, the presently disclosed invention relates to a method of inter-species genome transplantation, comprising: preparing a donor genome from a first species; preparing a recipient cell from a second species, wherein the first species and the second species are both from the same genus; and installing of the isolated donor genome into the recipient cells, whereby the donor genome phenotypically transforms the recipient cell to that of the first species. The donor genome can be isolated from cells of a first species or prepared synthetically. The donor genome can optionally contain a selection marker. In one aspect of the invention, proteins are removed from the donor genome prior to installation. In another aspect of the invention, the recipient cell comprises a recipient genome. The donor genome can encode a restriction endonuclease that recognizes sequences in the recipient genome but not the donor genome. The donor genome can be methylated, for example, the donor genome can be GATC Dam methylated. In still another aspect of the invention the first species is *Mycoplasma mycoides* Large Colony (LC) and the second species is *Mycoplasma capricolum.*

Another embodiment of the invention relates to a method for genome installation in a minicell, comprising: preparing a donor genome from a first species; preparing a recipient minicell from a second species, wherein the first species and the second species are both from the same genus; and installing the donor genome in the recipient minicell, whereby the donor genome phenotypically transforms the recipient cell to that of the first species. The donor genome can be isolated from cells of a first species or prepared synthetically. The donor genome can optionally contain a selection marker. In one aspect of the invention, proteins are removed from the donor genome prior to installation. In still another aspect of the invention the first species is *Mycoplasma mycoides* Large Colony (LC) and the second species is *Mycoplasma capricolum.*

BRIEF DESCRIPTION OF THE DRAWINGS

FIG. 1 shows various restriction modification systems.

FIG. 2 shows methylated genomic DNA.

FIG. 3 shows methylated genomic DNA in contrast to the methylated genomic DNA shown in FIG. 2.

FIG. 4 shows phase contrast micrographs of *mycoplasma* cells with altered cell shape due to the overexpression of FtsZ.

FIG. 5 shows phase contrast and epifluorescence micrographs of *mycoplasma* cells overexpressing the FtsZ protein, resulting in elongated cells that may be used as recipients in the transplantation of donor genomes.

FIG. 6. Enhanced transplantation of *M. mycoides* LC genomic DNA in the presence of the restriction enzyme Mbo I. Purified *M, mycoides* LC genomic DNA was mixed with serial dilutions of restriction enzyme Mbo I, the mixtures were transplanted into *M. capricolum* recipient cells, and transplants were recovered by plating on selective media. Natural methylation of the donor *M, mycoides* genomic DNA prevents it from being cleaved by the enzyme. In contrast, the genomic DNA of the recipient *M. capricolum* cells is sensitive to Mbo I. Co-transplantation of the donor DNA and the enzyme selectively compromises the genomic DNA of the recipient cells and this is reflected in the number of transplants recovered. This mechanism is consistent with the fact that transplant yield increases with increasing enzyme concentration. Plate numbers are listed on the bottom of the graph. Plate 1, no added genomic DNA; plate 2, no recipient cells; plate 3, genomic DNA plus 10 μl of Mbo I; plate 4, genomic DNA plus 1 μl of Mbo I; plate 5, genomic DNA plus 0.1 μl of Mbo I; plate 6, genomic DNA plus 0.01 μl of Mbo I; plate 7, genomic DNA without Mbo I.

FIG. 7. Demonstration that the DNA in the blocks was intact and circular, while the DNA in the band that migrated into the gel was linear. (A) A pulsed field gel loaded with plugs containing *M. mycoides* LC DNA. The 0.5×TBE buffer gel was electrophoresed for 20 hours and then stained with SYBR gold. The marker lane contains BioRad *Saccharomyces cerevisiae* genomic DNA size markers. Note the large amount of DNA remaining in the plugs. (B) The plugs are shown either before PFGE (BPFGE) or after PFGE (APFGE) and the genome size band produced after PFGE, and either with or without treatment with the Plasmid-Safe DNA nuclease. The nuclease enzyme digests linear DNA but has no effect on circular duplex DNA. These data indicate the band of DNA that migrated into the gel was exonuclease sensitive and therefore linear.

FIG. 8. Southern blot analysis of *M. capricolum, M. mycoides* LC and a series of transplant clones. Genomic DNA was digested with HindIII and electrophoresed on a 1% agarose gel. The DNA was transferred to an N+ nylon membrane and probed with an IS1296 specific probe. The additional IS1296 bands in transplant may result from a sudden expansion of the IS element when it was moved into the M. capricolum milieu upon transplantation.

Figure 9:
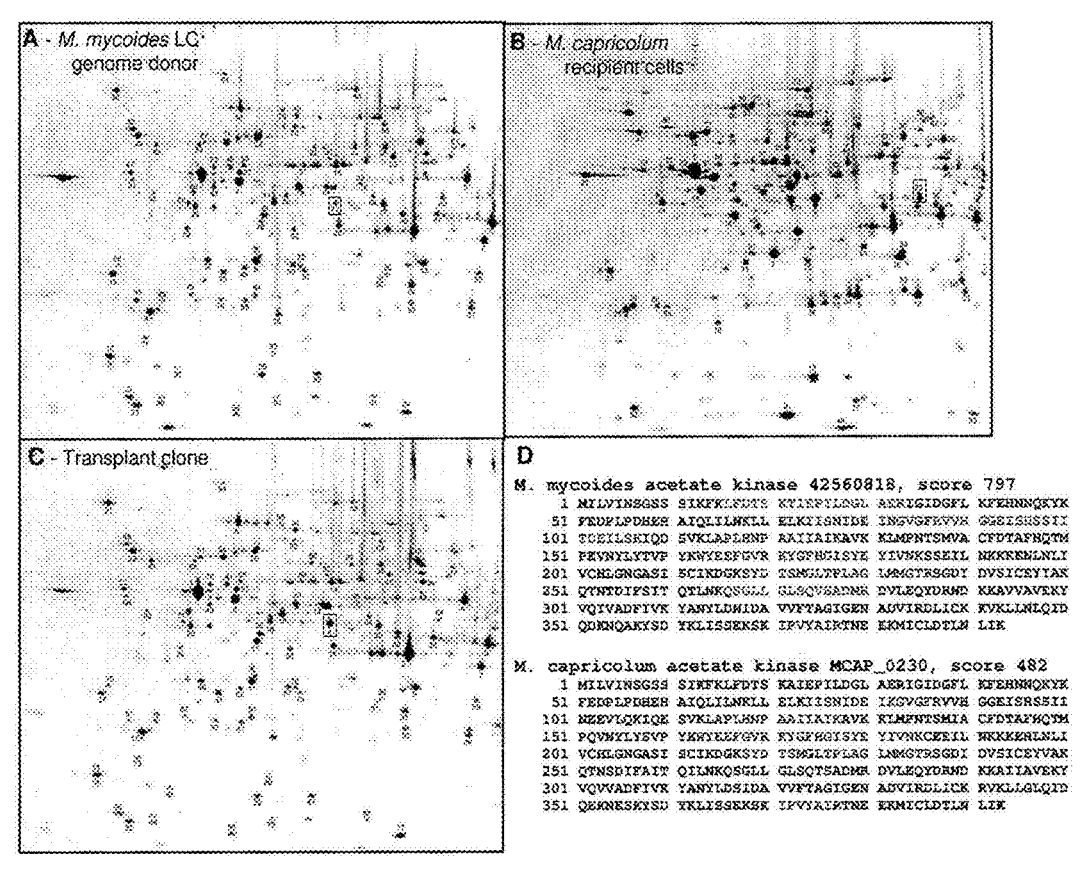

FIG. 9. Proteomic Analysis. 2-Dimensional gels were run using cell lysates from M. mycoides LC (A), M. capricolum (B) and a transplant clone (C). Standard conditions were used for the separation of protein spots in the first dimension on immobilizing pH gradient (IPG) strips (pH range 4 to 7) and in the second SDS-PAGE dimension (Mr 8 to 200 kDa) (18). The gels were stained with Coomassie Brilliant Blue G-250 and 96 spots were excised from each of the gels. Spots 71 (gel A), 23 (gel B) and 8 (gel C) were identified as acetate kinase. M. capricolum acetate kinase showed a clear alkaline pH shift (gel B). The sequence coverage map for trypsin-digested and MALDI mass spectrometry analyzed (MALDI-MS, ABI4700 Proteomics Analyzer) peptides of acetate kinase (spot 8, gel C) localizes peptides identical to the two Mycoplasma species (in red) and peptides present only in M. mycoides LC (in blue).

Figure 10:
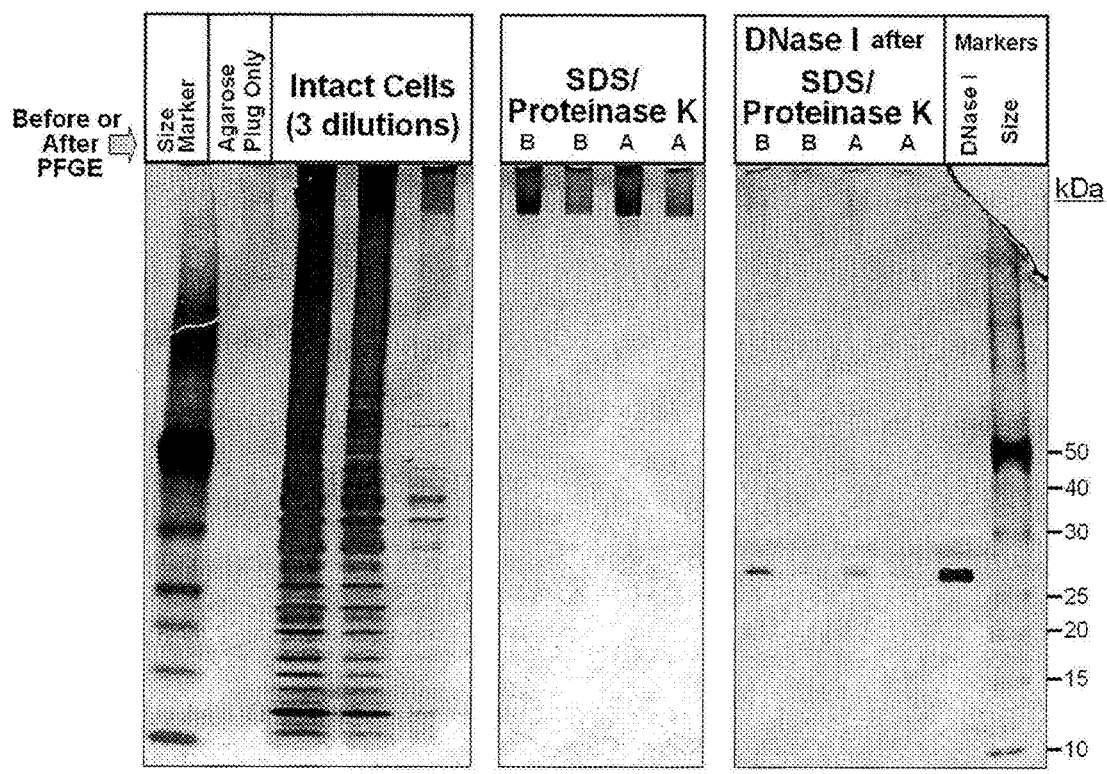

FIG. 10. SDS polyacrylamide gel electrophoresis analysis of isolated M. mycoides LC DNA in agarose blocks to show there were no detectable levels of protein associated with the DNA. The gels were silver stained. In the panel on the left the 3 lanes labeled "Intact Cells" were three dilutions of M. mycoides LC cells that were boiled in SDS and loaded onto the gel. The middle panel contains agarose blocks with the M. mycoides LC DNA that were boiled in SDS and loaded on the protein gel either before (B) or after (A) PFGE. To determine if the material at the top of the gel was protein or DNA in the panel on the right the before and after PFGE blocks were treated with DNase I. In that panel one of the markers was DNase I.

Figure 11:
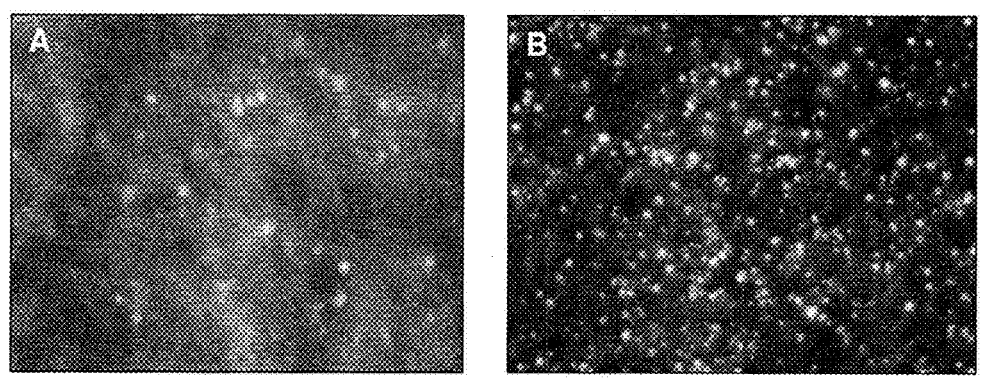

FIG. 11. Effect of streptomycin on M. mycoides LC donor genomic DNA topology before transplantation. Genomic DNA was gently isolated from M. mycoides LC cells as described in the text. Cells were grown in SP4 medium supplemented with tetracycline (10 µg/ml) (A) or tetracycline (10 µg/ml) and streptomycin (10 µg/ml) (B). The deproteinized DNA was stained with SYBR gold (1×; Molecular Probes) for 15 minutes at room temperature. Seven microliters of cells were loaded on a glass slide and visualized by fluorescent microscopy (×1000) (Zeiss Axioskop 2 plus).

Figure 12:
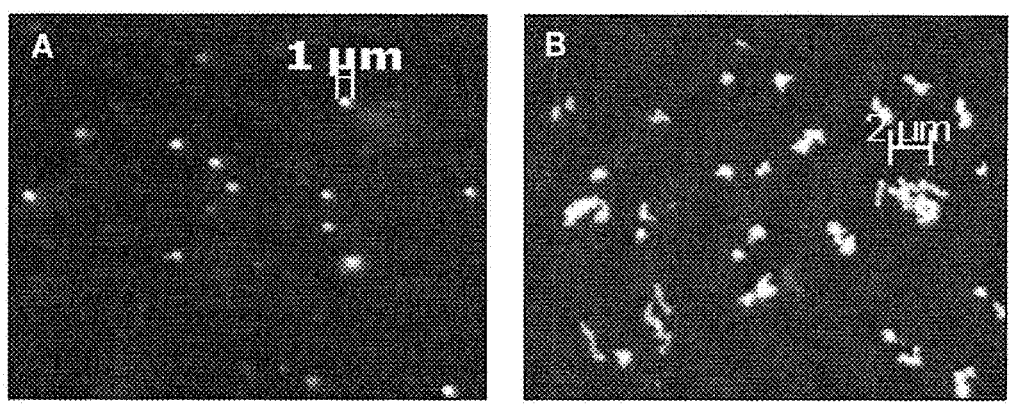

FIG. 12. Effect of pH on the shape of M. capricolum recipient cells grown in SOB medium supplemented with 17% fetal calf serum and 0.5% glucose when the pH was 7.5 (A) or 6.2 (B) after 18 hours of growth at 37° C. 500 µl of cells were centrifuged for 5 minutes at 2200 g at 10° C. and resuspended them in 200 µl PBS. Cells were stained for 15 minutes at room temperature by addition of SYBR gold (1×; Molecular Probes). Seven microliters of cells were loaded on a glass slide and visualized by fluorescent microscopy (×1000) (Zeiss Axioskop 2 plus).

FIG. 13. M. capricolum and M. mycoides LC specific PCR amplification of both wild type strains and a transplant (CL11.1).

Figure 14:
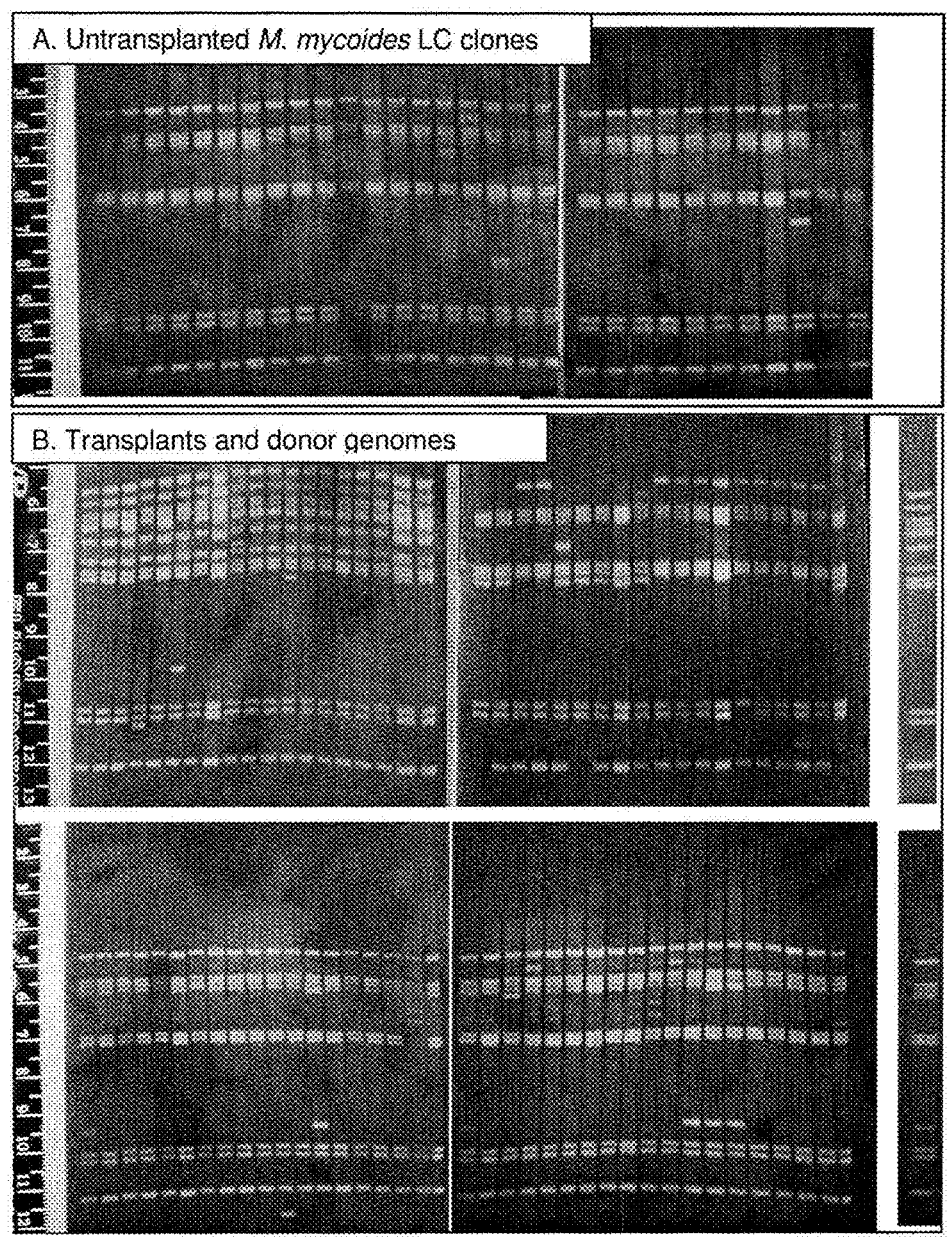

FIG. 14. Southern blots of 30 different M. mycoides LC filter clones (A) and ~50 transplants (B). The blots were probed with a PCR amplicon that hybridized to the IS1296 insertion sequences. Different samples, while all having the multiple copies of the IS1296, had slightly different patterns on the blots indicating movement of the element. For the transplants the donor genomes are shown in the single lanes.

FIG. 15. Colony hybridization of the M. mycoides LC (genome donor), M. capricolum (recipient cell) and transplants from four different experiments that were probed with a polyclonal antibody specific for the M. capricolum VmcE and VmcF surface antigens or with monoclonal antibodies specific for the M. mycoides LC VchL surface antigen.

DETAILED DESCRIPTION OF THE INVENTION

The chemical synthesis of a genome has recently been described. Gibson, et al., "Complete Chemical Synthesis, Assembly, and Cloning of a Mycoplasma genitalium Genome," Science (29 Feb. 2008) Vol. 319. no. 5867, pp. 1215-1220, and U.S. provisional application Nos. 61/062, 214 filed Jan. 23, 2008, 61/023,392 filed Jan. 24, 2008, 60/978,388 filed Oct. 8, 2007, and 60/983,549 filed Oct. 29, 2007, all of which are incorporated by reference in their entirety. This methodology is useful for a number uses, including as a means for testing hypotheses concerning the minimal set of genes required for cellular life as well as for constructing customized synthetic genomes which contain selected genes to encode desirable metabolic pathways. Once the synthetic genome is constructed, it must be introduced into a cellular milieu where the encoded instructions of the genome can be expressed. The presently disclosed invention demonstrates that a genome isolated from one species (the donor) can be transplanted into suitably prepared cells of a second species (the recipient). Introduction of the donor genetic material into the recipient host cell effectively converts the recipient host cell into a new cell that, as a result of the operation of the donated genetic material, is functionally classified as belonging to the genus and species of the donor genetic material.

Any genus and species of donor and recipient cells can be used with the disclosed methods. Optimally the donor chromosome is derived from a source organism that is of the same genus as the recipient host cell. For example, donors from various Mycoplasma species can be used to supply the genetic material for use with the disclosed invention either directly (in the form of a genome isolated from a natural source) or indirectly (where the genome is prepared synthetically and built upon a Mycoplasma precursor).

The disclosed invention relates to the transplantation of a donor genetic material into a recipient host cell, where the donor genetic material is functional and dominates the recipient host cell. Domination of the recipient host cell can be achieved through a number of different methods. The methods can be divided into two general categories, methods for use with recipient cells that retain their genome, and methods for use with recipient cells lacking an endogenous genome.

Supplanting Endogenous Host Genomes

Transplantation methods using recipient cells containing an endogenous genome preferably include a method by which the endogenous genome is inactivated by one or more products encoded by the donor genome. According to various exemplary methods provided herein, a donor chromosome or genome is prepared and introduced into the host cell. The donor genome may encode one or more systems which, upon introduction into the recipient cell, serve to inactive or otherwise destroy the recipient genome. A variety of systems are contemplated for use to achieve this goal. For example, restriction endonucleases can be encoded by the donor genome or chromosome that have specificity for the recipient genome. Other systems, such as inhibitory RNAs that prevent reproduction or function of the recipient genome can also be included. An example of such an inhibitory RNA would be one targeted to the recipient genome's origin of replication. Production of this inhibitory RNA by the donor prevents replication of the endogenous chromosome, which in turn allows for the donor genome to take control of the recipient cell and provide the genetic material for incorporation into daughter cells.

In one embodiment of the invention, the donor genome encodes one or more restriction endonuclease whose action is blocked or inhibited relative to the donor genome but is functional against the endogenous recipient genome. For example, it is possible to select a restriction endonuclease that cuts at very rare sites and to tailor a donor genome or chromosome that lacks those sites. In a preferred embodiment, this blocking is achieved by methylation of the donor genome. In another embodiment, the donor genome or chromosome may be methylated before or after installation or transplantation of the donor chromosome into a host or recipient cell. Further, methylation of the donor chromosome may occur naturally or artificially, such as in an in vitro environment.

An endogenous chromosome in a recipient cell may be unmethylated and/or inappropriately methylated, as in methylated at sites that do not protect the genome from endonuclease activity. Upon expression of the restriction enzyme from the donor chromosome, the restriction enzyme may cleave the resident chromosome at specific sites. In a further method, an appropriate restriction endonuclease is included in the transplantation process. The restriction endonuclease initiates degradation of the resident chromosome immediately after or nearly immediately after introduction of the restriction endonuclease into the host cell, saving time in comparison to the time required for the expression of the restriction endonuclease from the donor genome.

Methyl directed endonucleases (capable of cutting methylated DNA) may be employed by producing a methylase within the recipient cell and producing or co-transplanting the methyl directed restriction enzyme from or with the donor chromosome.

In some embodiments, the recipient is sensitive to a restriction endonuclease because it contains recognition sites for the enzyme. The donor chromosome would not have such sequences but would produce the enzyme, be co-transplanted with the enzyme, or the recipients could be pre-treated with the enzyme. Similarly, co-transformation of chemioenzymatic nucleases, chemical nucleases and modification reagents that target sequences specific to the resident chromosome may be used. All or some of these approaches may be formulated to selectively compromise a resident chromosome before, during and/or after transplantation. The range of available restriction endonucleases and meganucleases, together with the production of enzymes with tailored recognition sites, makes this approach widely applicable.

Alternatively, recipient cells maybe in the presence of nucleotide analogs and thus such analogs may only be present within the resident chromosome. Subsequently the analogs may be targeted by an agent encoded by or co-transformed with the donor chromosome. The resident chromosome is selectively compromised with or without the presence of a genetic ability to repair such lesions.

According to various methods provided herein, *Mycoplasma mycoides* LC encodes multiple restriction modification systems, most of which are different from the single restriction modification system in *M. capricolum* (FIG. 1). Although both *M. mycoides* LC and *M. capricolum* contain methylated adenines in their genomic DNA as determined by the recognition of an antibody specific for methylated adenine in Western blot analysis (FIG. 2), *M. mycoides* LC appears to be site-specifically methylated at GATC sequences by an ortholog of the *Escherichia coli* methylase encoded by the dam gene (Dam methylase), whereas *M. capricolum* is not. The Dam methylase transfers a methyl group from S-adenosylmethionine to the N6 position of the adenine residues in the sequence GATC. The viability of this system and method is evidenced by two factors; first, the susceptibility of *M. mycoides* LC genomic DNA to the restriction endonuclease DpnI which cleaves specifically at adenine-methylated GATC sequences and resistance to the restriction enzyme MboI which is blocked by adenine-methylation at GATC sequences; and second, the resistance of *M. capricolum* genomic DNA to DpnI and susceptibility to MboI (FIG. 3).

In some embodiments, one or more restriction endonucleases of the donor genome that are not present in the resident genome cleave the resident genome. For example, when an *M. mycoides* LC genome, which is GATC Dam methylated is transplanted into an *M. capricolum* cell, which is not GATC Dam methylated, expression of the *M. mycoides* LC restriction enzyme transcribed from the transplanted genome that cleaves unmethylated GATC sequences results in the resident *M. capricolum* genome being cut into many pieces. The transplanted *M. mycoides* LC is then free to commandeer the ghost *M. capricolum* cell. Other restriction endonucleases of *M. mycoides* LC not present in *M. capricolum* may also cleave the resident genome.

Efficient genome transplantation of natural or synthetic *M. genitalium* genomes (or other genomes, natural or synthetic) may be achieved according to one method provided herein by supplying the genome with an appropriate restriction modification system. This method may be performed in two steps. First, clone an *E. coli* Dam methylase gene into the *M. genitalium* genome, so that the resulting *M. genitalium* cells have genomes that are Dam methylated. Second, add a gene of the corresponding restriction endonuclease to the methylase containing clone. Although this example involves *E. coli* genes, the restriction-methylation system may be from a variety of organisms. Such engineered genomes are methylated and protected from their own restriction system. Transplantation into a sensitive strain lacking appropriate methylation causes the degradation of the resident chromosome. For synthetic genomes, where the genome is assembled within a host organism (and inactive), methylation of the synthetic genome may be provided by the host cloning strain. According to an alternative system and method, methylation may be performed in vitro before transplantation, or a donor genome may be synthesized so that it is resistant to the relevant restriction endonuclease. It will be appreciated that the resistance of a donor genome may be achieved by other methods and remain within the scope of the various methods provided herein.

Recipient cell genomes may also be rendered incapable of replication by exposition the recipient cells to various compounds or stimuli. For example, recipient cells can be exposed to compounds that cross link or otherwise render the recipient genome incapable of replicating but are then subsequently removed from system. Recipient cells can also be irradiated, thereby rendering the endogenous genomes incapable of replication but still capable of supporting the function of the transplanted donor chromosome.

A resident chromosome, according to a further system and method, may be selectively compromised without substantial alteration. Appropriately placed lox-P sites may selectively remove critical replication components from the resident chromosome—such as the origin and terminus of replication. While the chromosome remains substantially intact, it replicates poorly, if at all. In comparison, a donor chromosome free of such recognition sites may be more readily copied in the presence of Cre lox-P recombination. Sites other than the origin or terminus may similarly cause a resident chromosome to lose its capacity to replicate or function efficiently and thereby compromise it. Similarly the expression of a small RNA may produce quiescent E. coli. This RNA interferes with replication. Donor chromosomes may be made insensitive to this RNA or similar agents. In such a case, expression or co-transplantation of the RNA from or with the donor-insensitive chromosome selectively compromises replication of the resident chromosome without significantly altering the chromosome itself. The T4-phage Ndd protein also prevents E. coli chromosomes from functioning properly, however, the chromosomes remain fundamentally unaltered. The protein does not have a similar effect on the phage genome. Proteins such as Ndd may be used to selectively stop the replication of a resident chromosome, without affecting the capacity of a donor chromosome to be copied.

Achromosomal Host Cells

An alternative embodiment of the presently described invention calls for the use of achromosomal host or recipient cells. Achromosomal cells, also known as minicells, are typically products of aberrant cell division, and contain RNA and protein, but little or no chromosomal DNA. Minicells are derivatives of cells that lack chromosomal DNA and which are sometimes referred to as anucleate cells. Because eubacterial and archeabacterial cells, unlike eukaryotic cells, do not have a nucleus (a distinct organelle that contains chromosomes), these non-eukaryotic minicells are more accurately described as being "without chromosomes" or "achromosomal," as opposed to "anucleate." Nonetheless, those skilled in the art often use the term "anucleate" when referring to bacterial minicells in addition to other minicells. Accordingly, in the present disclosure, the term "minicells" encompasses derivatives of eubacterial cells that lack a chromosome; derivatives of archeabacterial cells that lack their chromosome(s), and anucleate derivatives of eukaryotic cells. It is understood, however, that some of the relevant art may use the terms "anucleate minicells" or anucleate cells" loosely to refer to any of the preceding types of minicells. Minicells, or ghost cells have several advantages over recipient cells retaining their endogenous genomes or artificial cell-like structures, such as liposomes, in that the cytoplasm of the minicell contain the enzymatic machinery to permit and direct protein synthesis from an exogenous genome or artificial chromosome.

A variety of bacteria have been shown to produce minicells. For example, U.S. Pat. No. 4,190,495, which is hereby incorporated by reference in its entirety, is drawn to minicell producing strains of E. coli that are stated to be useful for the recombinant expression of proteins. U.S. Pat. No. 7,183,105, which is also hereby incorporated by reference in its entirety, describes the production of eubacterial minicells and their use as vectors for nucleic acid delivery.

A minicell or ghost cell may be used as a recipient cell for receiving a donor genome and producing daughter cells expressing the donor genome. This process is limited, if not prevented, however, when a recipient cell that has been targeted as the ghost cell synthesizes a restriction nuclease that degrades the donor genome. Consequently there is a need for methods for genome installation for ghost cell generation and for daughter cell production.

Minicells are incapable of division or growth, but still contain a functioning cell wall, cell membrane, ribosomes, energy generating system, and are able to maintain the integrity of those systems for a long period of time. According to one system and method provided herein, mycoplasma minicells may be produced through disruption or over expression of some of the genes involved in chromosomal segregation (SMC, scpA, scpB, gyrB) and cell division (ftsZ). For instance, the ftsZ genes as found in M. genitalium, M. capricolum, and/or Mycoplasma allagatoris is cloned into shuttle plasmids containing oriC regions from each of these mycoplasmas. Over-expression of FtsZ protein leads to the appearance of small—chromosomeless cells, together with filamentous cells of variable length (FIG. 4, FIG. 5).

Additionally, a wide range of pre-treatments may be used with some or all of the methods that could be formulated to destroy a resident chromosome before transplantation, including those involving methylation or psoralen treatment. Any genetic, chemical or physical methods for destroying or inactivating the resident chromosome fall within the scope of the invention.

In yet another system and method, a temperature sensitive DNase may be utilized to degrade a recipient cell genome at one temperature, and then the DNase is rendered inactive at a second temperature used for transplantation. Similarly, a chromosome destruction f method may employ a reversible DNase (colicin E2). This enzyme and its homologs are readily inactivated by an immunity protein. Activation, production or addition of colicin E2 in a recipient cell degrades its genome while subsequent activation, production or addition of the corresponding immunity protein protects donor chromosomes added later.

While various embodiments and methods have been described herein, it should be understood that they have been presented by way of example only, and not limitation. Further, the breadth and scope of a preferred embodiment should not be limited by any of the above-described exemplary embodiments.

Commercial Utility

The capacity to synthesize whole bacterial genomes has recently been reported. Using this technology it is now possible to synthesize genomes that encode metabolic pathways capable of producing a variety of products for commercial use, such as vaccines, biofuels, and industrially useful enzymes.

The presently described technology is useful to produce immunological compositions to elicit an immune response from an organism. For example, the presently described technology can be used to produce vaccine compositions. The most effective vaccines have always employed live cells or viruses. Consider polio, vaccinia, or BCG. Strains of some bacterial pathogens such as Streptococcus pneumoniae or Salmonella sp. have immunogenic features that could make them effective vaccines; however, to date it has not been possible to effectively rid those organisms of their pathogenicity while retaining their immunogenicity. The task is too complicated for current genome manipulation technology. There are too many genes of unknown function and known function that need to be deleted or inactivated from the potential vaccine genomes. Gene removal would need to be done individually and in combinations. To do the work there are simply too many possibilities to test.

Using synthetic genomics technology, genomes could be assembled combinatorially from synthetic cassettes comprising individual genes or genome regions from a given organism, such that thousands of different variations of a genome are generated. This process could be a combination of specific deletions and random deletions. These populations of different genomes could be transplanted into suitable recipient cells, and the transplants screened in in vitro and/or in vivo assays that looked for immunogenicity and lack of pathogenicity. Thus, more vaccine candidates could be created and screened for appropriate activities in a rapid, inexpensive manner than could be done using non-synthetic genomics technology.

The methods described herein can be used to produce compositions effective to treat or prevent the disease contagious bovine pleuro pneumonia (CBPP), which is caused by the bacterium *Mycoplasma mycoides* Small Colony. This disease, also known as lung plague, is a major pathogen of cattle, yaks, buffalo, and zebu. The disease is widespread in Africa, the Middle East, Southern Europe, as well as parts of Asia. There is a real need for an improved vaccine. The disease organism is a close phylogenetic relative of the bacterium used here to demonstrate genome transplantation, *M. mycoides* Large Colony strain GM12. *M. mycoides* Small Colony is not readily amenable to genomic manipulation. A variety of antigen genes from the *M. mycoides* Small Colony bacterium could be cloned into the *M. mycoides* Large Colony genome using the synthetic genomics technology used to create the synthetic *M. genitalium* genome described earlier. The described methods could transplant many different versions of the *M. mycoides* Large Colony genome to which are added *M. mycoides* Small Colony genes and produce *M. mycoides* Large Colony cell that express selected *M. mycoides* Small Colony antigens. A variety of different *M. mycoides* Small Colony antigen genes individually and in combination are contemplated for use. Some of these mutants will function as live vaccines.

The presently disclosed methods are also useful for developing biofuels. Some eukaryotic algae synthesize as much as 70% of their dry weight as oils. These oils, which are the product of photosynthesis, could be ideal biofuels. Organisms that produce these oils could be grown in ponds in deserts so no arable croplands would be lost to biofuel production. One problem with these algae is they grow slowly. Using genome assembly technology, we could clone the genes that encode the enzymes that make up these pathways and remodel the genes to allow prokaryotic instead of eukaryotic gene expression by changing transcriptional promoters, translation signals, and codon optimization. These cassettes of genes encoding metabolic pathways could be built into the genomes of photosynthetic bacteria so that the resulting chimeric genomes might produce the same oils as a result of photosynthesis. Those genomes would then be transplanted into appropriate recipient cells.

The disclosed invention also has utility regarding the production of industrial enzymes or industrial organisms. The disclosed methods can be used to build a genome that is a chimera of *Clostridium acetobutylicum* and *Clostridium cellulolyticum* that has the genes from the former species that encode the enzymes needed to synthesize ethanol from glucose and genes from the latter species that encode cellulases that can efficiently degrade cellulose. That genome could be transplanted into a suitable recipient cell to produce a cell that could efficiently degrade cellulose to produce the ethanol.

The following examples are offered to illustrate but not to limit the invention.

Example 1

Transplantation of a *Mycoplasma mycoides* Large Colony (LC) Genome into a *Mycoplasma capricolum* Recipient Cells

*Mycoplasmas*, members of the class Mollicutes, were selected for building a synthetic cell. This choice was based on a number of characteristics specific to this bacterial taxon. The essential features of *mycoplasmas* are small genomes, use of UGA to encode tryptophan (rather than a stop codon) by most species and the total lack of a cell wall. A small genome is easier to synthesize and less likely to break during handling. The altered genetic code facilitates cloning in *E. coli* because it curtails the expression of *mycoplasma* proteins. The absence of a cell wall makes the exterior surfaces of these bacteria similar to the plasma membranes of eukaryotic cells, and may simplify our task of installing a genome into a recipient cell by allowing us to use established methods for insertion of large DNA molecules into eukaryotic cells.

Our synthetic genome will be based on *Mycoplasma genitalium*, which has the smallest genome (580 Kb) of any cell that has been grown in axenic culture(2, 3). Although our synthetic genome is modeled on the *M. genitalium* chromosome, the genome installation methods were developed using two faster growing *mycoplasma* species, *Mycoplasma mycoides* subspecies *mycoides* Large Colony strain GM12 and *Mycoplasma capricolum* subspecies *capricolum* strain California kid, as donor and recipient cells respectively. These organisms are both opportunistic pathogens of goats, but can be grown in the laboratory under BL2 conditions. They divide every 80 and 100 minutes respectively; whereas *M. genitalium*, the organism used to model a recently published synthetic genome on, divides only every 9-10 hours. Use of these faster growing *mycoplasmas* accelerated our task of developing methods for transplantation of a synthetic *M. genitalium* genome.

*M. mycoides* LC and *M. capricolum* are distinct species within the *Mycoides* subgroup of *mycoplasmas*. Both genomes were sequenced to determine the degree of relatedness. Comparison of the two genomes showed 76.4% of the 1,083,241 bp draft sequence of the *M. mycoides* LC genome can be mapped to the 1,010,023 bp *M. capricolum* genome (Genbank accession number NC 007633.5), and this content matches on average at 91.5% nucleotide identity. The remaining ~24% of the *M. mycoides* LC genome contains a large number of insertion sequences not found in *M. capricolum*. This whole genome shotgun project has been deposited at DDBJ/EMBL/GenBank under the project accession AAZK00000000. The version described in this example is the first version, AAZK01000000.

A number of methods were explored to achieve this inter-species genome transplantation. The process had three key phases: (1) isolation of intact donor genomes from *M. mycoides* LC, (2) preparation of recipient *M. capricolum* cells, and (3) installation of the isolated genome into the recipient cells. This direction of genome transplantation was selected based on the observation that plasmids containing a *M. mycoides* LC origin of replication (oriC) can replicate in *M. capricolum* while plasmids with an *M. capricolum* oriC will not replicate in *M. mycoides* LC.

Donor Genomic DNA Preparation.

Manipulation of whole chromosomes in solution exposes the DNA to shear forces that can cause breakage. Thus it was important to minimize genome manipulation during the detergent and proteolytic enzyme treatments by suspending the cells in agarose blocks. Intact chromosomes were immobilized in the resulting cavern in the agarose that originally held the cell. Digested protein components, lipids, RNAs, and sheared genomic DNAs could then be dialyzed or electrophoresed away from the immobilized intact genomic DNA.

Whole intact genomic DNA isolation was performed using a CHEF MAMMALIAN GENOMIC DNA PLUG KIT from BIO-RAD. Briefly, *M. mycoides* LC cells were grown containing tetracycline resistance (tetM) and betagalactosidase genes (lacZ) at 37° C. to moderate density in SP4 medium supplemented with 10 μg/ml of tetracycline and 10 μg/ml of streptomycin. Addition of streptomycin to the medium will be discussed later. Fifty to 100 ml of cultured cells were pelleted by centrifugation at 4,575 g for 15 minutes at 10° C. The cells were re-suspended in 20 ml of 10 mM Tris pH 6.5 plus 0.5 M sucrose, pelleted as before, and re-suspended again in 1 ml (−1 to $5\times10^9$ cells/ml). The cell suspension was incubated for 15 minutes at 50° C. then mixed with an equal volume of 2% low-melting-point (LMP) agarose in 1×TAE buffer [40 mM Tris-acetate, 1 mM EDTA]. After 5 minutes at 50° C., the mixture of cells and LMP agarose (2 ml) was distributed in 100 pl aliquots into plug molds. The 20 plugs solidified at 4° C. Embedded *mycoplasma* cells were lysed and proteins digested at 50° C. for 24 hours by addition of 6 ml proteinase K reaction buffer [100 mM EDTA, pH 8.0, 0.2% sodium deoxycholate; 1% sodium—lauryl sarcosine] with 240 pl proteinase K. The 20 plugs were then washed 4 times at room temperature for 1 hour in 20 ml of 1× TE buffer [Tris-HCl (20 mM)-EDTA (50 mM); pH 8.01 with agitation and stored in 10 ml of TE buffer at 4° C.

To confirm that the gentle preparation of the genomic DNA yielded intact circular molecules. Some agarose plugs were subjected to pulsed field gel electrophoresis (PFGE) in a 1% LMP gel in TAE, with contour-clamped homogeneous electric field (CHEF DR.III; BIO-RAD). Pulse times were ramped from 60 to 120 seconds over 24 hours at 3.5 V/cm. After migration, plugs were removed from the wells and stored in 10 ml of [Tris-HCl (20 mM)-EDTA (50 mM); pH 8.01 buffer at 4° C. until used as source of intact genomic DNA for chromosome transplantation experiments. During PFGE it is possible that intact circular bacterial chromosomes become caught in the agarose and do not migrate, while full length linearized DNA, as well as smaller DNA fragments, RNAs, proteins, and any other charged cellular molecules remaining after the detergent and enzyme digestion electrophoresed out of the plug. A SYBR gold (Molecular Probes) stained pulsed field gel, presented FIG. 7A, showed a band of DNA that co-electrophoresed with a 1.125 MB linear DNA size marker (approximately the same size as the *M. mycoides* LC genome), plus an intense band at the position of the wells, suggesting a large amount of DNA was still in the plugs. Extensive digestion of the plug and the excised 1.125 MI3 band with Plasmid-Safe ATP-dependent DNAse (EPICENTRE BIOTECHNOLOGIES) left the amount of DNA in the plug relatively unchanged, whereas the DNA in the 1.125 MB band was degraded (FIG. 7B). Plasmid-Safe ATP-Dependent DNase digests linear double-stranded DNA to deoxynucleotides and, with lower efficiency, closed-circular and linear single-stranded DNA. The enzyme has no activity on nicked or closed-circular double-stranded DNA or supercoiled DNA. This indicates there was a large amount of circular genomic DNA in the plug.

The plugs were analyzed to confirm the DNA encased in them was naked. Plugs loaded SDS polyacrylamide gels after being boiled in SDS showed no detectable levels of protein indicating at least the vast majority of the DNA was naked (FIG. 10). Further evidence of the efficiency of our deproteinization of the chromosomes comes from mass spectrometry analysis, which is a more sensitive technique. No *M. mycoides* LC peptides were in agarose plugs before PFGE and barely detectable amounts of a few different *M. mycoides* LC peptides in the plugs after PFGE. Different plugs had different peptides.

The final step in donor genome preparation entailed liberation of the DNA from agarose encasement. Prior to transplantation experiments the agarose plugs containing *M. mycoides* LC genomic DNA (before or after PFGE) were washed 2 times 30 minutes in 1 ml of 0.1× TE buffer [Tris-HCl (2 mM)-EDTA (5 mM); pH 8.01 with gentle agitation. The buffer was completely removed and the agarose plugs were melted at 65° C. with 1/10th volume of 10× beta-agarase Buffer [10 mM bis Tris-HCl (pH 6.5), 1 mM EDTA] for 10 minutes. The molten agarose was cooled to 42° C. during 10 minutes and incubated overnight with 2.5 units of beta agarase I (NEW ENGLAND BIOLABS) per 100 μl of plug at the same temperature. Each plug was calculated to contain approximately 10 μg of DNA (−$8\times10^9$ genomes). In sum, these data suggested that the plugs contained large amounts of intact, circular, supercoiled, and naked genomic DNA from *M. mycoides* LC.

Preparation of donor genomic DNA from *M mycoides* LC cells grown in medium containing the aminoglycoside antibiotic streptomycin doubled the efficiency of genome transplantation. The streptomycin, which can induce genome compactness, altered the appearance of the donor genomes. Fluorescent micrographs of donor DNA isolated h m cells grown without streptomycin show a mish-mash of DNA fibers mixed with few bright dots (FIG. 11A). When *M. mycoides* LC cultures were grown in SP4 medium with streptomycin, the kaction of the DNA visible as bright dots rather than fibers was much greater (FIG. 11B). It is believed that the bright dots may represent a circular supercoiled form of the genome.

Recipient Cell Preparation and Genome Transplantation Reaction Conditions.

*M. capricolum* recipient cells were prepared in a 6 ml culture of SOB medium containing 17% fetal calf serum and 0.5% glucose that was incubated at 37° C. until the medium pH was 6.2, then pelleting the cells by centrifugation at 4,575 g 15 minutes at 10° C. It was found that additional growth further acidified the medium resulting in recipient cells that were much less competent for genome transplantation. As pH decreased from 7.4 to 6.2, regular ovoid *M. capricolum* cells, changed shapes dramatically. Cells are longer, thinner and branched (FIG. 12). Cells were washed once [Tris 10 m.M-NaCl 250 m.M (pH 6.5)], resuspended with 200 μl of $CaCl_2$ (0.1 M), and held on ice for 30 minutes. During that period, 20 μl of beta-agarase treated-plugs (~50 ng/μl) were delicately transferred into 400 μl of SP4 medium without serum (SP4 (−)), using wide bore genomic pipette tips and incubated 30 minutes at room temperature. For the genome transplantation, *M. capricolum* cells mixed with 10 μg of Yeast tRNA (Invitrogen) were gently transferred into the 400 μl SP4 (−) containing 20 μl of *M. mycoides* LC whole genomic DNA. An equal volume of 2× fusion buffer [Tris 20 mM, NaCl 500 mM, $MgCl_2$ 20 mM, polyethylene glycol 8000 (PEG) 10%] was added, and the contents were mixed by rocking the tube gently for a minute. After 50 minutes at 37° C., 10 ml of SP4 was added, and cells were incubated for 3 hours at 37° C. to allow recovery. Finally, cells were centrifuged at 4,575 g IS minutes at 10° C., resuspended in 0.7 ml of SP4 and plated on SP4 agar plates containing 3 μg/ml tetracycline and 150 μg/ml X-Gal. Treatment with other antibiotics such as antibiotic chloramphenicol and streptomycin has also been observed to significantly increase the efficiency of transplantation.

The plates were incubated at 37° C. until large blue colonies, putatively *M. mycoides* LC, formed after ~3 days. To minimize the risk of contaminating our transplant cultures with *M. mycoides* LC cells from the donor genome preparation process three different hoods were used for the cell culture work: one for *M. mycoides* LC donor cell preparation, one for *M. capricolum*, and one for working with transplant clones. Sometimes, after ~10 days smaller colonies, putatively *M. capricolum*, both blue and white, were visible. Individual colonies were picked and grown in broth medium containing 5 µg/ml of tetracycline. During propagation, the tetracycline concentration was progressively increased to 10 µg/ml. When first developed, this technique subjected all plugs to PFGE, later it was found this step was unnecessary. No significant difference was observed in transplantation yield as a result of PFGE of the plugs.

In every experiment two negative controls were included. To ensure that the *M. mycoides* genomic DNA contained no viable cells, one control was processed exactly as described above except no *M. capricolum* recipient cells were used. Similarly, in another control, *M. capricolum* recipient cells were mock transplanted without using any donor DNA. The results of a series of experiments are shown in Table 1. No colonies were ever observed in controls lacking recipient cells, thus the donor DNA was free of any viable contaminating *M. mycoides* LC cells.

TABLE 1

Results of a series of experiments showing controls.

| | Number of colonies | | | |
|---|---|---|---|---|
| | Negative controls | | | |
| Experiment date | No Donor DNA control colonies | No recipient cell control colonies | *M. mycoides* LC transplant colonies | Total *M. capricolum* recipient cells |
| Mar. 28, 2006 | 0 | 0 | 1 | $4 \times 10^9$ |
| Apr. 13, 2006 | 2 | 0 | ~65 | $8 \times 10^8$ |
| Apr. 19, 2006* | 0 | 0 | 1 | $1 \times 10^8$ |
| May 25, 2006 | 0 | 0 | 1 | $6 \times 10^8$ |
| Jun. 07, 2006 | 0 | 0 | 16 | $5 \times 10^8$ |
| Jun. 08, 2006 | 0 | 0 | 17 | $2 \times 10^8$ |
| Jun. 28, 2006 | 0 | 0 | 8 | $7 \times 10^8$ |
| Jul. 06, 2006 | 0 | 0 | 3 | $6 \times 10^9$ |
| Sep. 07, 2006 | 0 | 0 | 2 | $3 \times 10^{10}$ |
| Nov. 17, 2006† | 0 | 0 | ~100 | $2 \times 10^8$ |
| Nov. 24, 2006† | 0 | 0 | ~100 | $5 \times 10^8$ |
| Dec. 13, 2006 | 0 | 0 | 20 | $4 \times 10^8$ |
| Jan. 04, 2007 | 0 | 0 | 17 | $5 \times 10^7$ |
| Jan. 18, 2007 | 0 | 0 | 20 | $2 \times 10^7$ |
| Mar. 01, 2007 | 0 | 0 | 24 | $6 \times 10^7$ |
| Mar. 20, 2007† | 0 | 0 | 134 | $5 \times 10^7$ |
| Mar. 21, 2007† | 0 | 0 | 81 | $3 \times 10^7$ |
| Mar. 29, 2007† | 0 | 0 | 132 | $2 \times 10^7$ |

*After this experiment 6 experiments were performed but not listed here that produced no transplant clones.
†The higher genome transplantation efficiency in these experiments was attributed to the inclusion of streptomycin in the SP4 medium used to grow the *M. mycoides* LC donor genomes.

Analysis of Putative Transplants

The blue, tetracycline resistant colonies resulting from *M. mycoides* LC genome transplantation were to be expected if the genome was successfully transplanted. However, colonies with that phenotype could also result from recombination of a fragment of *M. mycoides* LC genomic DNA containing the tetM and lacZ genes into the *M. capricolum* genome. To rule out recombination, the phenotype and genotype of the transplanted clones were examined.

Genotype Analysis

Figure 8:
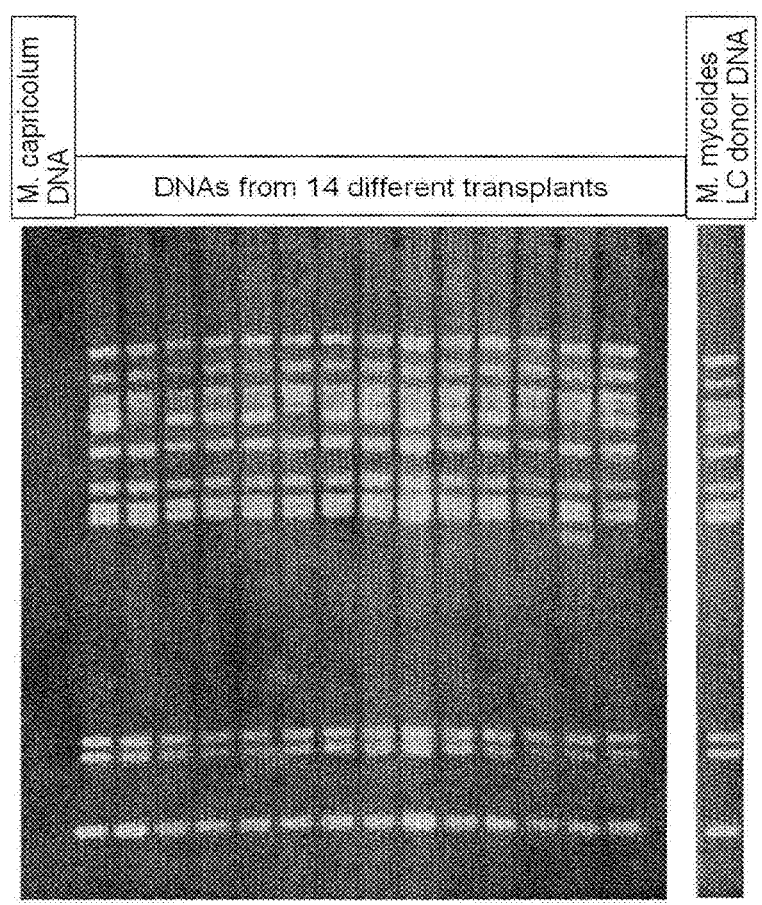

Several transplant clones were analyzed by PCR using primers specific for each species to determine if the putative transplants had *M. mycoides* LC sequences other than the selected tetM and lacZ marker genes. PCR primers specific were used for IS1296 insertion sequences, which are present in eleven copies in the sequenced *M. mycoides* LC genome but are absent in the *M. capricolum* genome. Similarly, PCR primers specific for the *M. capricolum* arginine deiminase gene were used, which is not present in *M. mycoides* LC. The IS1296 PCR produced an amplicon only when the template was the *M. mycoides* wild type strain or was one of the transplanted clones. Similarly, the *M. capricolum* arginine deiminase PCR generated an amplicon when using *M. capricolum* template DNA but not when using *M. mycoides* LC wt DNA or DNAs from transplant clones. The PCR experiments left open the possibility that fragments of the *M. mycoides* LC genome containing an IS1296, the tetM gene, and the lacZ gene had recombined into the *M. capricolum* genome in such a way that they destroyed the arginine deiminase gene (FIG. 13). A more convincing genotypic analysis that looked at the overall genome used Southern blot analysis of the donor and recipient *mycoplasmas* and a series of putative transplants. Genomic DNA from each of those species was digested with the restriction enzyme HindIII and run on a 1% agarose gel. Southern blots were prepared and probed with IS1296 sequences. As expected, no probe hybridized to the wild type *M. capricolum* lane (FIG. 8). This analysis was performed on every transplant obtained (>200), as well as a series of *M. mycoides* LC clones (FIG. 14). It was observed that while many Southern blots of the wild type *M. mycoides* and putative transplants were identical, a number showed variations in the banding patterns. It was assumed that this was the result of IS element transposition. Analysis of blots with 30 untransplanted *M. mycoides* LC samples and with 71 transplants shows more diversity in the IS1296 containing fragments in the transplants. It was hypothesized that while mobility of the IS1296 element may be somewhat suppressed in *M. mycoides* LC cells, there may be no suppression in the initial phase of a transplant as the donor genome was introduced into the *M. capricolum* cytoplasm. Next sample sequencing of whole genome libraries generated from two transplant clones was performed. The analysis of more than 1300 sequence reads from the genome of each clone (>1× genome coverage) showed all reads matched *M. mycoides* LC sequence. There was no sequence that was unique to *M. capricolum*. Of the 24 reads that did not match the *M. mycoides* LC or *M. capricolum* genome sequences, most were either very short reads (<200 bases) or the result of chimeric clones, which is to be expected due to the active transposons in *M. mycoides* LC and also as part of library construction. The above results were all consistent with the hypothesis that the *M. mycoides* LC genomes was successfully introduced into *M. capricolum* followed by subsequent loss of the *capricolum* genome during antibiotic selection.

Phenotype Analysis

The phenotype of the transplanted clones was examined in two ways. One looked at single gene products characteristic for each of these two *mycoplasmas*. Using colony-Western blots, donor and recipient cell colonies and colonies from four different transplants were probed with polyclonal antibodies specific for the *M. capricolum* VmcE and VmcF surface antigens and with monoclonal antibodies specific for the *M. mycoides* LC VchL surface antigen. In both assays the transplant blots bound the *M. mycoides* LC VchL specific antibody with the same intensity as *M. mycoides* LC VchL bound the *M. mycoides* LC blots (FIG. 15). Similarly, the transplant blots did not bind the antibodies specific for the *M. capricolum* VmcE and VmcF. In addition, cell lysates of all three strains were subjected to proteomic analysis using differential display in 2-dimensional electrophoresis (2-DE) gels followed by identification of proteins spots using matrix-assisted laser desorption ionization (MALDI) mass spectrometry. Strikingly, the 2-DE spot patterns of the *M. mycoides* LC and the transplanted clone were identical within the limits of 2-DE, while the *M. capricolum* 2-DE spot patterns were very different. More than 50% of the respective spots could not be matched among the gels (FIG. 9A-C). More evidence that the transplant proteome was identical to the *M. mycoides* LC proteome and did not have any *M. capricolum* features was gained from MALDI-MS data. For nearly 90 identified spots of the transplant, confidence scores obtained with the Mascot algorithm were invariably equal or higher for *M. mycoides* LC than for *M. capricolum* proteins, despite high sequence homologies. Ninety-four MS/MS scores were obtained that uniquely matched peptide sequences in *M. mycoides* LC proteins (Mascot expect values between 0.11 and $3.8 \times 10^{-11}$), No peptides uniquely matched *M. capricolum*. In an example, FIG. 9D visualizes peptides in acetate kinase matching only the sequence of the respective *M. mycoides* LC protein. Thus the phenotypic assays were also consistent with the transplants being *M. mycoides* LC, and not the result of a *M. capricolum*-*M. mycoides* LC mosaic produced by recombination between the donor and recipient cell genomes after the transplantation of the *M. mycoides* LC genome and before the two genomes segregate upon cell division.

Optimization of Genome Transplantation Efficiency

To determine what factors govern genome transplantation efficiency, the number of *M. capricolum* recipient cells and the amount of *M. mycoides* LC genomic DNA used in transplantation experiments was varied. Transplant yield was optimal when $10^7$-$5 \times 10^7$ cells were used. At lower donor DNA concentrations there was a linear relationship between the amounts of genomic DNA transplanted and transplant yield. That yield plateaued at higher donor DNA concentrations (Table 2). In later experiments it was found that substitution of 5% PEG 6000 (Fluka) for 5% PEG 8000 (USB), as used in the experiments described above, resulted in an approximately 5× increase in transplantation efficiency (Table S3). It was also observed that RNase treatment of the donor genomes did not eliminate transplantation.

TABLE 2

Genome transplantation as a function of the amount of *M. mycoides* LC genomic DNA transplanted.

| | Number of colonies | | | |
| --- | --- | --- | --- | --- |
| | Negative controls | | | |
| ng *M. mycoides* LC genomic DNA | Colonies on no recipient cell controls | Colonies on mock transplanted controls | Transplant colonies* | Total *M. capricolum* recipient cells |
| 102.3 | 0 | 0 | 90/101 | $5 \times 10^8$ |
| 46.8 | 0 | 0 | 72/81 | $5 \times 10^8$ |
| 25.7 | 0 | 0 | 54/67 | $5 \times 10^8$ |
| 10.9 | 0 | 0 | 25/6 | $5 \times 10^8$ |
| 4.1 | 0 | 0 | 5/6 | $5 \times 10^8$ |
| 1.3 | 0 | 0 | 2/2 | $5 \times 10^8$ |

*Transplant colonies observed on two different plates.

TABLE S3

Effect of PEG source and molecular weight on genome transplantation efficiency.

| | Number of colonies | | |
| --- | --- | --- | --- |
| | Negative controls | | |
| PEG molecular weight and manufacturer | Colonies on no recipient cell controls | Colonies on mock transplanted controls | Transplant colonies* |
| PEG 200 (Fluka) | 0 | 0 | 0 |
| PEG 400 (Fluka) | 0 | 0 | 0 |
| PEG 600 (Fluka) | 0 | 0 | 0 |
| PEG 1000 (Fluka) | 0 | 0 | 0 |
| PEG 2000 (Fluka) | 0 | 0 | 2 |
| PEG 4000 (Fluka) | 0 | 0 | 74 |
| PEG 6000 (Fluka) | 0 | 0 | 218 |
| PEG 6000 (USB) | 0 | 0 | 85 |
| PEG 8000 (Fluka) | 0 | 0 | 72 |
| PEG 8000 (USB) | 0 | 0 | 44 |
| PEG 10,000 (Fluka) | 0 | 0 | 8 |
| PEG 20,000 (Fluka) | 0 | 0 | 0 |

These data demonstrate the transplantation of whole genomes from one species to another with the resulting progeny being the same species as the donor genome. However they do not explain the mechanism of the transplant. Because *mycoplasmas* are similar to mammalian cells due to their lack of a cell wall, a series of approaches were tried that are effective for transferring large DNA molecules into eukaryotic cells. These included cation-detergent mediated transfection, electroporation, and compaction of the donor genomes using various cationic agents. While none of those approaches proved effective for whole genome transplantation, the PEG-based method may be akin to PEG-driven cell fusion methods developed for eukaryotic cells. To test this hypothesis, two parental strains of *M. capricolum*, one carrying a tetM marker in the chromosome and the other one with the chloramphenicol resistance marker (CAT) in a stable oriC plasmid, were both prepared as "recipient" cells, mixed and incubated in the presence of the fusion buffer as described above for transplantation experiments. Progeny resistant to both antibiotics with a low frequency only in the presence of 5% PEG were obtained. The number of colonies increased approximately 30× when cells were pre-treated with $CaCl_2$ (Table S4). Sequencing analysis of 30 clones showed all had both the tetM and CAT markers in the cells at the expected chromosomal and plasmid locations. Thus, it was concluded that under our PEG-based method, *M. capricolum* cells fuse. Those results agree with Shlomo Rottem's membrane studies demonstrating that fusion of *M. capricolum* cells was maximal in 5% PEG. Gene transfer into *Mycoplasma pulmonis* was also mediated by PEG at concentrations likely to fuse cells, albeit only small DNA segments are transferred. One can imagine that in some instances the cells may fuse around the naked *M. mycoides* LC genomes. Those genomes, now trapped in *M. capricolum* cytoplasm express the tetM protein allowing the large fused cells to grow and divide once plated on the SP4 agar containing tetracycline. Cells lacking the *M. mycoides* genome do not grow. Eventually, now in the absence of PEG and through a process of cell division and chromosome segregation, normal albeit tetracycline resistant, beta-galactosidase producing *M. mycoides* cells produce large blue colonies on the plate. This basic approach of PEG mediated genome transplantation may allow other species to be transplanted with naked genomes containing antibiotic resistance genes. The literature suggests that partial digestion of the cell wall in more conventional bacteria to make protoplasts or spheroplasts renders them amenable to the incorporation of large amounts of foreign DNA. Nonetheless, this kind of whole genome transfer is unlikely to occur in nature. It was observed that in the absence of SDS and proteinase K treatment, nucleoids from *M. mycoides* LC cells would not produce transplants until they had been deproteinized. Given the improbability of free-floating bacterial genomes that are both deproteinized and intact occurring naturally, genome transplantation could be a phenomenon unique to the laboratory. Still a fifth form of bacterial DNA transfer was discovered that permits recipient cells to be platforms for the production of new species using modified natural genomes or manmade genomes generated by the methods being developed by synthetic biologists.

TABLE S4

Cell fusion in *M. capricolum*

| Number of *M. capricolum* recipient cells exposed to fusion procedure | | | Number of colonies tet$^R$ and CAT$^R$ |
|---|---|---|---|
| *M. cap* clone 1.1B (CAT) | *M. cap* clone 297 (tetM) | Protocol | |
| 3.8 × 10$^8$ | 1.6 × 10$^8$ | 5% PEG method$^a$ | 173 |
| 3.8 × 10$^8$ | 1.6 × 10$^8$ | 5% PEG method + DNase I$^b$ | 189 |
| 3.8 × 10$^8$ | 1.6 × 10$^8$ | 5% PEG method w/o PEG$^c$ | 0 |
| 3.8 × 10$^8$ | 1.6 × 10$^8$ | 5% PEG method w/o CaCl$_2$$^d$ | 6 |
| 3.8 × 10$^8$ | — | 5% PEG method | 0 |
| — | 1.6 × 10$^8$ | 5% PEG method | 0 |

$^a$The two parental strains were prepared simultaneously as "recipient" cells as described previously for genome transplantation experiment and mixed in the presence of the 2X fusion buffer [Tris 20 mM, NaCl 500 mM, MgCl$_2$ 20 mM, polyethylene glycol 8000 (PEG) 10%]
$^b$Addition of 10 units of DNase I (New England Biolabs) in the PEG-cell mixture to demonstrate colonies due to cell fusion not the uptake of extracellular plasmid DNA.
$^c$The two parental strains were treated as described in (a) however the 2x fusion buffer did not contain any PEG [Tris 20 mM, NaCl 500 mM, MgCl$_2$ 20 mM]
$^d$The two parental strains were treated as described in (a) but the CaCl2 treatment was omitted. Cells were pre-incubated 30 minutes on ice in the washing buffer [Tris 10 mM pH6.5: NaCl 250 mM].

What is claimed is:

1. A method for transplantation of a *Mycoplasma mycoides* Large Colony donor cell genome in a recipient *Mycoplasma capricolum*, said method comprising:

(a) isolating a closed circular double stranded donor genome from a *Mycoplasma mycoides* Large Colony donor cell and suspending the isolated donor genome in agarose;

(b) deproteinizing the donor genome and liberating the donor genome from the agarose;

(c) preparing a *Mycoplasma capricolum* as a recipient cell for introduction of the donor genome by removing or inactivating the recipient cell genome, and simultaneously introducing the isolated donor genome from step (b) into the recipient cell in presence of polyethylene glycol, wherein the donor genome phenotypically transforms the recipient cell to that of the of *Mycoplasma mycoides* Large Colony.

2. The method of claim 1, wherein the donor genome comprises a selection marker.

3. The method of claim 1, wherein the donor genome encodes a restriction endonuclease that recognizes sequences in the recipient genome but not the donor genome.

4. The method of claim 1, wherein the donor genome is methylated.

5. The method of claim 4, wherein the donor genome is GATC Dam methylated.

\* \* \* \* \*